United States Patent [19]

Weitmann et al.

[11] Patent Number: 4,680,965
[45] Date of Patent: Jul. 21, 1987

[54] PROCESS FOR CONTINUOUS DENSITY MEASUREMENT

[75] Inventors: Heinz Weitmann, Rosenfeld; Alfred Keller, Leinfelden-Echterdingen, both of Fed. Rep. of Germany

[73] Assignee: Weitmann & Konrad GmbH & Co. KG, Leinfelden-Echterdingen, Fed. Rep. of Germany

[21] Appl. No.: 798,129

[22] Filed: Nov. 14, 1985

[30] Foreign Application Priority Data

Nov. 29, 1984 [DE] Fed. Rep. of Germany ....... 3443511

[51] Int. Cl.⁴ .............................................. G01N 9/12
[52] U.S. Cl. ........................................ 73/445; 73/452; 73/453
[58] Field of Search ................. 73/445, 452, 453, 434; 137/91, 238

[56] References Cited

U.S. PATENT DOCUMENTS

| | | | |
|---|---|---|---|
| 1,589,418 | 6/1926 | Woidich | 73/445 |
| 2,023,196 | 12/1935 | Fairchild | 73/445 |
| 3,908,466 | 9/1975 | Bell | 73/452 |
| 4,103,552 | 8/1978 | Bucchianeri et al. | 137/240 |
| 4,257,442 | 3/1981 | Claycomb | 137/238 |

FOREIGN PATENT DOCUMENTS 283593  4/1915  Fed. Rep. of Germany ........ 73/445

*Primary Examiner*—John Chapman
*Attorney, Agent, or Firm*—Shenier & O'Connor

[57] ABSTRACT

A process for the continuous measurement of the density of a liquid by means of an aerometer body swimming in the liquid is characterized by the feature that the liquid is allowed to flow periodically at an increased flow rate past the aerometer body in order to clean the same of foreign matter, gas bubbles or the like disturbing the measuring, with the measuring procedure being interrupted during this cleaning period. In an apparatus for performing this process, an aerometer body is surrounded in a measuring vessel by a partition wall at a small distance therefrom, and line is provided, through which liquid to be measured may be introduced at a relatively high flow rate into the space between the aerometer body and the partition wall in order to periodically clean the aerometer body.

3 Claims, 1 Drawing Figure

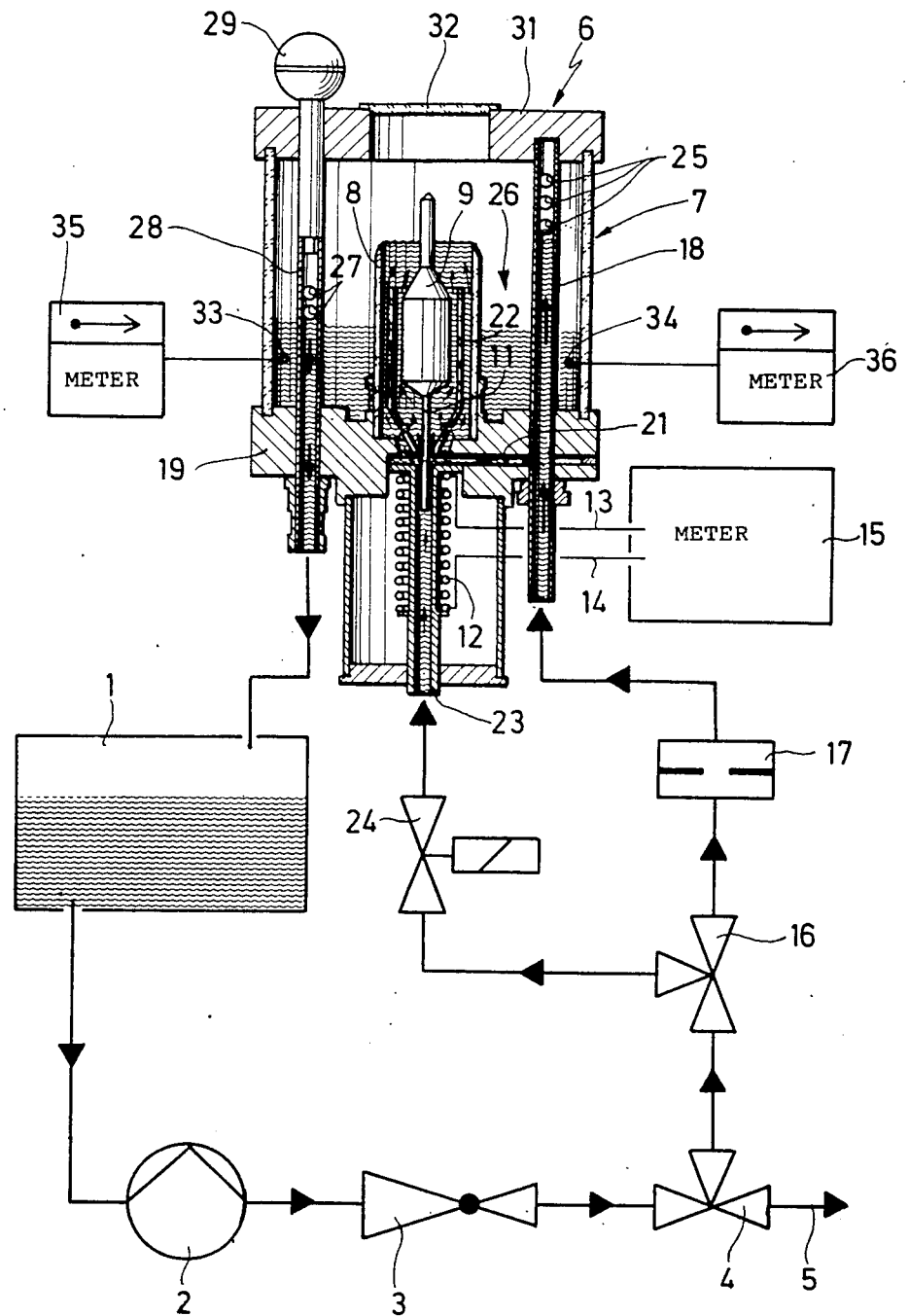

PROCESS FOR CONTINUOUS DENSITY MEASUREMENT

The invention relates to a process for the continuous measurement of the density of a liquid flowing slowly through a measuring vessel by means of an aerometer body swimming in the liquid.

In known processes of this kind, in particular, in the measurement of liquids containing foreign matter such as fibers, gas bubbles or the like, there is the difficulty that this foreign matter disturbs the measurement result. The foreign matter adheres to the aerometer body and influences its buoyancy, which results in the indication of false measurement values.

The object underlying the invention is to remedy this deficiency and to indicate a process which enables continous, precise measurement of the density of a liquid, and, more particularly, also if the liquid contains foreign matter such as suspended materials, gas bubbles or the like.

The object is attained in accordance with the invention in that the liquid is allowed to flow periodically at an increased flow rate past the aerometer body in order to clean the same of foreign matter, gas bubbles and the like disturbing the measurement, and in that the measuring procedure is interrupted during this cleaning period.

An apparatus for performing this process with a measuring vessel and an aerometer body swimming in the same comprises a partition wall surrounding the aerometer body in the measuring vessel at a small distance therefrom and also a line for introducing liquid to be measured into the space between the aerometer body and the partition wall.

The following description of a preferred embodiment serves in conjunction with the appended drawing, in which a density measuring apparatus is schematically illustrated, to explain the invention in greater detail.

From a container 1, liquid is withdrawn by a pump 2 and conducted via a pressure reducing straightway valve 3 and a T-piece 4 in the direction of the arrow 5 to a consumer (not illustrated), for example, an offset printing machine. For the purpose of continuously monitoring the density of this liquid fed to the consumer, part of it is branched off via the T-piece 4 as liquid to be measured and fed to a density measuring device (aerometer) which is designated in its entirety in the drawing by the reference numeral 6.

The measuring device 6 includes a measuring vessel 8 which is arranged in an external vessel 7 and into which the liquid to be measured is introduced in such a manner, which is to be described hereinafter, that it flows slowly through the measuring vessel. A conventional aerometer body 9 making the actual density measurement and carrying at its lower end a downwardly protruding iron pin 11 swims in the measuring vessel 8. The iron pin 11 is enclosed by the windings of a coil 12 which is connected via lines 13, 14 to an electronic evaluation instrument 15. Depending on the density of the liquid to be measured in the measuring vessel 8, the aerometer body 9 submerges more or less into the measuring vessel 8. The iron pin 11 which penetrates the coil 12 to a corresponding degree, alters the coil inductance which is determined, indicated and/or recorded in a manner known per se by the electronic evaluation instrument.

The liquid to be measured flows out of the T-piece 4 via a further T-piece 16 and a restrictor 17 limiting the quantity flowing through, into a riser 18, from which a branch-off line 21 extending in a bottom 19 of the external vessel 7 branches off to the bottom of the measuring vessel 8. The liquid to be measured flows out of this branch-off line 21 from the bottom, in the manner indicated by the small arrows, into the measuring vessel 8, to exit again at the upper edge of this vessel after the same has been completely filled, and enter the external vessel 7.

Stationarily arranged in the measuring vessel 8 is a partition wall 22 which surrounds the aerometer body 9 in an all around contactless manner at a small distance therefrom. The partition wall 22 tapers downwardly towards the iron pin 11 and also surrounds this pin at it exits from the measuring vessel in a contactless manner at a small distance therefrom. The bottom 19 of the external vessel contains in the area of the branch-off line 21 openings through which the liquid to be measured may flow out of the branch-off line 21 both into the area between the aerometer body 9 and the partition wall 22 and into the area between the measuring vessel 8 and the partition wall 22. In this way, the liquid to be measured is constantly flowing slowly through the measuring vessel 8, and a continous or periodic density measurement can be carried out in a manner known per se with the aid of the aerometer body 9 swimming in the liquid to be measured.

As illustrated, the partition walls 22 also comprises in its lower, conically shaped area apertures for liquid to be measured, through which the same may flow from the external side of the partition wall to its internal side.

The branch-off line 21 is furthermore connected to a pipeline 23 of larger cross-section than the branch-off line 21 which penetrates the coil 12 coaxially, The iron pin 11 submerges into the upper end of this line 23, Liquid to be measured may be fed from the T-piece 16 via a remote controlled, for example, magnetically actuated valve 24, into the pipeline 23. Since the connection line between the T-piece 16 and the pipeline 23 is similarly of a relatively large cross-section and does not have a restriction, a larger quantity of liquid to be measured may flow through it when the valve 24 is open than through the connection line between the T-piece 16 and the riser 18.

The riser, in turn, which similarly has a larger cross-section than the branch-off line 21 extends upwardly in the external vessel 7 and comprises bores 25, through which liquid to be measured which has not found its way into the measuring vessel 8 via the branch off line 21, enters the external vessel 7, where it forms a constantly regenerating supply 26 of liquid to be measured. The level of this supply 26 of liquid to be measured in the external vessel 7 is determined by ports 27 in a pipe-shaped discharge line 28. The pipe which forms the discharge line 28 is inserted in a sealed off and removable manner in the bottom 19 of the external vessel 7 so that the liquid supply may be drained off for the purpose of cleaning the apparatus. The pipe forming the discharge line 28 may be pulled out by manually engaging a knob 29 which is connected to the pipe and attached to the pipe above a wall 31 closing off the external vessel 7 at the top, with a cover 32. The wall of the measuring vessel 8, the side wall of the external vessel 7 and/or the cover 32 preferably consist of a transparent material, for example, glass or plastic to enable the flow conditions and the measuring procedure to be observed.

The liquid flows out of the discharge line 28 from the external vessel 7 and finally back into the container 1.

During the measuring procedure, the valve 24 is closed. The liquid to be measured flows via the restrictor 17, the riser 18 and the branch-off line 21 into the measuring vessel 8, where the density is measured with the aid of the aerometer body 9. If the liquid to be measured contains foreign matter such as, for example, fibrous suspended materials or gas bubbles, these easily become attached to the aerometer body 9 and alter its buoyant force, whereby the precision of the measurement is substantially impaired. In order to remove foreign matter adhering to the aerometer and falsifying the measurement result, the same is, without having to be removed from the measuring vessel 8, thoroughly rinsed with liquid to be measured, whereby adhering foreign materials are torn off. To this end, after interruption of the measuring procedure, i.e., switching-off of the electronic evaluation instrument 15, the valve 24 is opened to enable a strong current of liquid to be measured to flow via the line 23 from the bottom, into the measuring vessel 8, and, in particular, into the relatively narrow area between the aerometer body 9 and the partition wall 22. The liquid to be measured flows at a rapid rate, forming a strong current, past the aerometer body, and pulls off foreign matter adhering to the same, so that the body 9 cleaned in this manner again delivers precise measurement results. The liquid to be measured used for the cleaning similarly flows over the upper, free edge of the measuring vessel 8 into the external vessel 7 and from there returns to the container 1 via the ports 27 of the discharge line 28. After the aerometer body 9 has been cleaned, the valve 24 is closed again and the density measurement continued.

A large part of the liquid to be measured flows via the openings 25 of the riser 18 directly into the supply 26 of liquid to be measured without influencing the aerometer body 9. Since the riser 18 and also the discharge line 28 have a relatively large cross-section, comparatively large quantities of liquid to be measured may be branched-off at the T-piece 4 and fed to the measuring device 6. The same is, therefore, very sensitive to density changes of the liquid in the area of the T-piece 4 and shows a quick reaction.

The supply 26 of liquid to be measured constantly present between the external vessel 7 and the measuring vessel 8 may be used to measure further specification quantities or parameters of this liquid simultaneously with the density specification. The supply 26 may, for example, contain sensors 33, 34, known per se, for the electrical conductivity, the temperature and/or the pH value of the liquid to be measured, which are connected via measurement lines to evaluation instruments 35, 36.

The time intervals within which the measurement is interrupted and the apparatus is periodically cleaned by opening the valve 24, are determined by the degree of dirtiness of the liquid to be measured.

What is claimed is:

1. Apparatus for the continuous measurement of the density of a slowly flowing liquid, comprising an external vessel (7), a measuring vessel (8) inside the external vessel, the liquid to be measured flowing slowly through said measuring vessel and from there into said external vessel, an aerometer body (9) swimming in the liquid in said measuring vessel, a partition wall (22) between said measuring vessel and said aerometer body surrounding said aerometer body in an all around contactless manner, a first conduit (21) for supplying said slowly flowing liquid to be measured into said measuring vessel and to said aerometer body swimming therein, a second conduit (23) having a larger cross-section than the first conduit for also supplying liquid to be measured into said measuring vessel and to said aerometer body, said first and second conduits being connected to a common source (1) of said liquid to be measured, said second conduit including a valve (24) causing, when opened, a strong current of liquid to be measured to flow at a rapid rate via the second conduit into said measuring vessel and in the area between the aerometer body and the partition wall, said strong current when flowing past the aerometer body pulling off foreign matter adhering to the same.

2. Apparatus according to claim 1, characterized in that the measuring vessel (8) is surrounded by an external vessel (7) whose bottom (19) contains a riser (18) feeding said liquid and a discharge line (28) draining off the liquid, with an outlet opening (25) of the riser located higher than an overflow port (27) of the discharge line so that a supply (26) of liquid to be measured is formed in the measuring vessel (8), and in that the riser (18) is connected via a branch-off line (21) to the measuring vessel (8).

3. Apparatus according to claim 2, characterized in that measuring probes (33, 34) for determining further liquid parameters are arranged in the supply (26) of liquid to be measured formed in the external vessel (7).

* * * * *